(12) United States Patent
Morice

(10) Patent No.: US 6,680,074 B1
(45) Date of Patent: Jan. 20, 2004

(54) COMPOSITION COMPRISING PROPOLIS AND AT LEAST AN ESSENTIAL OIL

(76) Inventor: Andre Pierre Morice, 6, av Anatoie Franco, Lorient (FR)

( * ) Notice: Subject to any disclaimer, the term of this patent is extended or adjusted under 35 U.S.C. 154(b) by 0 days.

(21) Appl. No.: 09/463,156

(22) PCT Filed: Aug. 4, 1998

(86) PCT No.: PCT/FR98/01739

§ 371 (c)(1),
(2), (4) Date: Jan. 19, 2000

(87) PCT Pub. No.: WO99/07396

PCT Pub. Date: Feb. 18, 1999

(30) Foreign Application Priority Data

Aug. 11, 1997 (FR) ............................................. 97 10414
Feb. 19, 1998 (FR) ............................................. 98 02027

(51) Int. Cl.⁷ ............................................... A61K 35/78
(52) U.S. Cl. ....................................................... 424/725
(58) Field of Search ............................... 424/195.1, 725

(56) References Cited

U.S. PATENT DOCUMENTS 5,942,244 A  *  8/1999  Friedman et al. ........... 424/435
6,027,716 A     2/2000  Levin et al. .................. 424/58

FOREIGN PATENT DOCUMENTS

| EP | 0 747 057 | 12/1996 |
| RU | 2041937 | * 8/1995 |
| WO | WO 95/25084 | * 8/1995 |
| WO | WO 97/02040 | 1/1997 |

OTHER PUBLICATIONS

Database WPI, Sect. Ch, Week 9325, Derwent Pub. Ltd, London, GB; C1 B04, AN 93–203503, XP002083501 & RO 103 501A Mar. 25, 1992, abstract.

Gout, Mireille, Propolis, Its Properties and Its Use, Jun. 25, 1985, pp. 60–64, Thesis for the State Diploma of Doctor of Pharmacy.

* cited by examiner

*Primary Examiner*—Michael Meller
(74) *Attorney, Agent, or Firm*—Wolf, Greenfield & Sacks, PC

(57) ABSTRACT

The invention is directed to a composition including propolis, oregano and at least one essential oil and methods of making said composition. The compositions may be applied to the skin and/or mucous membranes and are useful for treating microbial infections including viral infections.

13 Claims, No Drawings

COMPOSITION COMPRISING PROPOLIS AND AT LEAST AN ESSENTIAL OIL

The present invention relates to a composition comprising propolis and at least one essential oil. It also concerns uses of this composition.

Propolis is a chemical substance synthesized by bees. It is present on the inner surface of beehive alveoli. Propolis is known for its antiviral properties.

Unfortunately, propolis does not have sufficient antiviral activity towards some viruses, such as viruses resistant to antiviral chemotherapy.

The need therefore exists for a composition having sufficient antiviral activity which may be used at very low doses.

The object of the invention is therefore a composition characterized in that it contains propolis and at least one essential oil.

The composition offers the advantage of using, at very low doses, two constituents of natural origin which are readily available and whose association shows excellent antiviral activity.

Another advantage lies in the fact that the composition, in addition to antiviral treatment, is able to treat conditions of bacterial and/or mycotic origin. The composition of the invention also offers the advantage of being easy to apply to the skin and/or mucous membranes or of being ingested by a living being.

A further object of the invention is use of a composition, as antiviral agent, containing propolis and at least one essential oil.

A third object of the invention is use of a composition containing propolis and at least one essential oil to produce a medicinal product intended for the treatment of bacterial diseases.

With this composition it is possible to treat diseases related in particular to the presence of non-enveloped DNA-containing viruses (adenoviruses), enveloped viruses such as herpesvirus or the HSV1 virus, or those related to the presence of papillomaviruses or non-enveloped RNA-containing viruses (type 2 poliovirus) or enveloped RNA-containing viruses.

A fourth object of the invention is use of a composition containing propolis and at least one essential oil to produce a medicinal product intended for the treatment of mycotic infections on the skin and/or mucous membranes.

This composition can be used in particular to treat infections related to the presence of staphylococci, β-hemolytic streptococci, entero bacteria (*E. Coli*), pyocyanic bacteria (*pseudomonas aeruginosa*).

Finally, a last object of the invention is use of a composition containing propolis and at least one essential oil to produce a medicinal product intended for the regeneration of skin and/or mucous membranes cells and tissues.

After being properly cleansed and therefore rid of its impurities, propolis is cold mixed with the essential oil.

The oil may be chosen from among chemically pure compounds. These compounds may preferably be chosen from among the aromatic compounds such as benzoic acids, benzaldehydes or alcohols of cinnamic acid, from among the flavonoids, terpenes such as β-bisabolol, α-acetoxy betulinol, from among esters, alcohols, oxides, aldehydes, ketones, lactones, phenols, from among other chemical molecules having similar or analogue physico-chemical characteristics, or even from among mixtures of these different chemical molecules.

The composition of the invention may contain a natural essential oil chosen from Oregano, Carvacrol Oregano, Clove, Sage, Thyme, *Melaleuca alternifolia, Melaleuca terpineol*, Cypress, Lemon Eucalyptus, *Eucalyptus dives, Eucalyptus radiata, Eucalyptus globulus*, odoriferous Verbena, *Rosmarinus officinalis*, balsam fir, balm fir, Provence Sage, *Cinnamomum zeylanicum, Cinnamomum chinensis*, Lavender, Verbena and their mixtures.

The essential oil is preferably in the quantity of 0.1% by weight relative to the total weight of the composition.

Propolis preferably comprises from 50 to 55% of resins and balsams, 30 to 40% wax, 5 to 10% essential oils, 5% pollen, 5% organic and mineral matter. Propolis is preferably in the quantity of 10% by weight relative to the total weight of the composition.

Also, the composition of the invention may comprise at least one additive chosen from among vitamins, trace elements, sugar, enzymes, alcohols, vaseline.

The composition of the invention may be in different galenical forms such as in suppository, ointment, tincture, inhalant, capsule, tablet, lotion, pessary form.

The composition of the invention may consist of a cosmetic and/or dermatological composition for the skin and/or mucous membranes.

The invention will be illustrated below with the following examples which are in no way restrictive.

The different concentrations are given in weight percentage.

EXAMPLE 1

| | |
|---|---|
| Propolis | 10.0 |
| Thyme | 0.1 |
| Lavender | 0.1 |
| Sage | 0.1 |
| Alcohol up to | 100.0 |

The composition is in the form of a tincture lotion intended for external use.

EXAMPLE 2

| | |
|---|---|
| Propolis | 10.0 |
| Thyme | 0.1 |
| Rosemary | 0.1 |
| Sage | 0.1 |
| Lavender | 0.1 |
| Vaseline up to | 100.0 |

This composition is in the form of an ointment intended for external use.

EXAMPLE 3

| | |
|---|---|
| Propolis | 10.0 |
| Melaleuca | 0.1 |
| Excipient up to | 100.0 |

This composition is in the form of a pessary intended for the treatment of vaginal infections.

EXAMPLE 4

| | |
|---|---|
| Propolis | 10.0 |
| Eucalyptus globulus | 0.1 |
| Excipient up to | 100.0 |

This composition is in the form of a suppository to treat infections of the respiratory tract.

EXAMPLE 5

| | |
|---|---|
| Propolis | 10.0 |
| Oregano carvacrol | 0.1 |
| Melaleuca terpineol | 0.1 |
| Savory | 0.1 |
| Clove | 0.1 |
| Sage | 0.1 |
| Excipient up to | 100.0 |

This composition is in the form of a lotion to treat bacterial and mycotic infections.

I claim:

1. An antiviral, antibacterial or antimycotic composition comprising effective amounts of propolis and essential oils of oregano, verbena, odoriferous verbena, balsam fir, *Melaleuca alternifolia, Melaleuca terpineol*, myrtle, and lemongrass.

2. Composition according to claim 1, further containing at least one oil selected from the group consisting of sage, lavender and their mixtures.

3. Composition according to claim 1, wherein the essential oil is present in a quantity of 0.1% by weight relative to the total weight of the composition.

4. Composition according to claim 2, wherein the propolis contains:

from 50 to 55% resins and balsams;
30 to 40% wax;
5 to 10% essential oils;
5% pollen;
5% organic and mineral matter.

5. Composition according to claim 1, wherein propolis is present in a quantity of 10% by weight relative to the total weight of the composition.

6. Composition according to claim 1, further comprising at least one additive selected from the group consisting of vitamins, trace elements, enzymes, sugar, alcohols, and vaseline.

7. Composition according to claim 1, wherein the composition is in a form selected from the group consisting of a suppository, ointment, tincture, inhalant, capsule, tablet, lotion, and pessary.

8. Composition according to claim 1, wherein the composition is in a form selected from the group consisting of a cosmetic and a dermatological composition.

9. A method for the production of a medicinal product, said method comprising:

placing the composition of claim 1 in a pharmaceutically acceptable carrier to prepare the medicinal product.

10. The method of claim 9, wherein the pharmaceutically acceptable carrier is suitable for administration to the skin.

11. The method of claim 9, wherein the pharmaceutically acceptable carrier is in a form suitable for administration to a mucous membrane.

12. A method for treating a viral infection, said method comprising administering a composition of claim 1 to the skin.

13. A method for treating a viral infection, said method comprising administering a composition of claim 1 to a mucous membrane.

* * * * *